United States Patent [19]
Filomio

[11] Patent Number: 6,139,516
[45] Date of Patent: *Oct. 31, 2000

[54] WRAPPING METHOD

[75] Inventor: Louise D. Filomio, 56 Hewitt Ave., Bronxville, N.Y. 10708

[73] Assignee: Louise D. Filomio, Bronxville, N.Y.

[ * ] Notice: This patent is subject to a terminal disclaimer.

[21] Appl. No.: 08/419,143

[22] Filed: Apr. 10, 1995

[51] Int. Cl.[7] ................................................ A61F 13/12
[52] U.S. Cl. .................................................... 602/74
[58] Field of Search ...................... 602/74–75; 128/857; 606/204.15, 204.25, 204.35

[56] References Cited

U.S. PATENT DOCUMENTS

| | | | |
|---|---|---|---|
| 1,110,772 | 9/1914 | Gunderman | 602/74 X |
| 4,717,735 | 1/1988 | Strem | 424/447 |
| 4,823,778 | 4/1989 | Ewing | 606/204.35 |
| 4,933,177 | 6/1990 | Grollier et al. | 424/74 |
| 4,954,532 | 9/1990 | Elliott et al. | 514/846 |
| 5,415,861 | 5/1995 | Duffy et al. | 424/401 |

*Primary Examiner*—Richard J. Apley
*Assistant Examiner*—Kim M. Lee

[57] ABSTRACT

A method of wrapping the head is provided in accordance with the invention. The method includes the steps of applying a detoxifying clay or mud to the face, wrapping a first bandage around the face, pulling the top of the wrapped bandage towards the back of the head, applying a second bandage around the forehead and face, leaving the bandages in place for a predetermined period of time, removing the bandages, and removing the clay or mud from the face.

9 Claims, 1 Drawing Sheet

WRAPPING METHOD

FIELD OF THE INVENTION

This invention relates generally to body wrapping and, in particular, to a method of wrapping the head.

BACKGROUND OF THE INVENTION

Body wrapping is the art of covering the human body with gauze bandages. This art has been practiced in Europe and the United States for many years.

In general, the bandages used for body wrapping are covered with clay or mud. Alternatively, the mud can be applied to the body prior to application of the bandages.

Body wrapping is used to achieve "immediate inch loss" by compacting fatty tissue of the body. In addition, body wrapping is practiced for its "detoxifying effect" specifically, its ability to extract toxins and waste of the body through the pores of the skin. Body wrapping also cleanses the elastin of the skin and the elasticin of the soft tissues, which results in a smoother appearance of the skin.

In general, body wrapping is often carried out by wrapping the entire body, including the head. Many times, however, it is desired to achieve toning or tightening at only one section of the body and therefore, only that portion of the body is wrapped.

Head wrapping is done for the specific purpose of improving the appearance of the face and neck. However, many times age lines, especially on the face, are not diminished entirely.

It would therefore, be desirable to provide a method of wrapping the head that diminishes age lines and firms the neck and jaw.

It is a goal of the present invention to provide an improved method of wrapping the head.

It is another goal of the invention to provide a method of wrapping the head that imparts a healthy glow to the face.

It is a further goal of the invention to provide a method of wrapping the head that noticeably diminishes age lines.

It is still another goal of the invention to provide a method of wrapping the head that firms the neck and jaw.

It is still a further goal of the invention to provide a method of wrapping the head that gives the face a subtle, younger look.

Still other goals of the invention will in part be obvious and will in part be apparent from the following detailed disclosure and the scope of the invention will be indicated in the claims.

SUMMARY OF THE INVENTION

Generally speaking, a method of wrapping the head is provided in accordance with the invention. The method includes the steps of applying a detoxifying clay or mud to the face, wrapping a first bandage around the face, pulling the top of the wrapped bandage towards the back of the head, applying a second bandage around the forehead and face, leaving the bandages in place for a predetermined period of time, removing the bandages, and removing the clay or mud from the face.

The invention accordingly comprises the several steps and the relation and order of one or more of such steps with respect to each of the others which are exemplified in the following detailed disclosure.

BRIEF DESCRIPTION OF THE DRAWINGS

For a fuller understanding of the invention, reference is made to the accompanying drawings, in which.

DETAILED DESCRIPTION OF THE PREFERRED EMBODIMENTS

The method of wrapping the head provided in accordance with the invention includes the steps of applying a detoxifying clay or mud to the face, wrapping a first bandage around the face, pulling the top of the wrapped bandage towards the back of the head, applying a second bandage around the forehead and face, leaving the bandages in place for a predetermined period of time, removing the bandages, and removing the clay or mud from the face.

The detoxifying clay or mud can be any type of sea clay mask or other composition commonly employed for this purpose. One suitable composition is disclosed, for example, in U.S. Pat. No. 4,717,735 issued to Richard C. Strem on Jan. 5, 1988. As disclosed therein, the composition includes a clay selected from the group consisting of bentonite and montmorillonite, and various inorganic salts such as magnesium sulfate, magnesium chloride, sodium chloride, and a minor amount of zinc oxide. However, it is understood that other suitable compositions are well known to those skilled in the art and the scope of the present invention is not limited by the particular detoxifying clay or mud that is selected.

The detoxifying clay or mud is applied to the face in an upward motion, i.e. towards the top of the head. This is important because the clay or mud should be applied against gravity. In a preferred embodiment, the clay or mud is also applied to the neck using a similar upward motion.

The head is wrapped after the detoxifying clay or mud mask is applied. Wrapping is accomplished using two rolled bandages. In a preferred embodiment, elasticized Ace® bandages are used. Such bandages are packaged in a rolled condition and are soaked in water or a suitable sea clay or mud in their rolled condition. After the bandages are soaked, the water, sea clay or mud is squeezed from the bandage until the bandage is nearly dry. At that point, the bandages are ready to be used in the wrapping method provided in accordance with the invention.

Figures 1, 2:
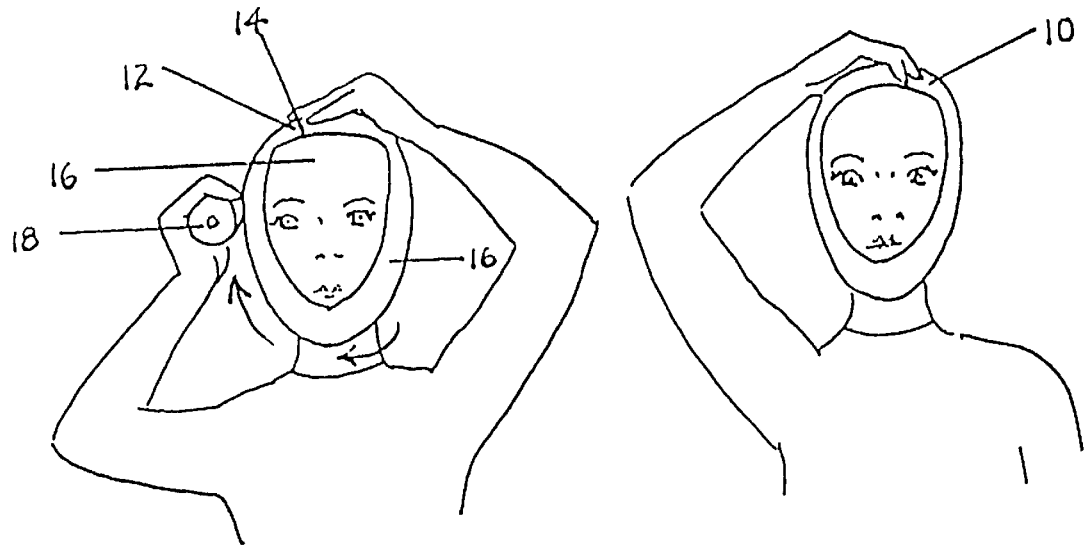
FIG. 1 illustrates the step of wrapping a first bandage around the face in accordance with the invention.
FIG. 2 illustrates the step of pulling the top of the wrapped bandage towards the back of the head in accordance with the invention.

The method of wrapping is illustrated in FIGS. 1–4. As shown in FIG. 1, the unrolled end of a first bandage 10 is held on the top of the head 12 with the left hand 14. The bandage 10 is then rolled around the face 16 and under the chin using the right hand 18 to progressively unroll the bandage 10. In a preferred embodiment, the bandage 10 is rolled around the face 16 and under the chin two times. Wrapping of the first bandage 10 is completed by unrolling the bandage 10 around the neck and tucking the loose end.

The bandage 10 is then pulled back towards the top of the head as shown in FIG. 2. The bandage 10 should be pulled with a firm, but gentle, motion. This serves to uplift laugh lines, crows feet, worry lines, as well as the cheeks and jaw line. Because the bandage is elastic, the skin is held taut, thereby smoothing the skin and allowing the "rejuvenated" elasticin to grab hold of the smoothed skin shape.

Figures 3, 4:
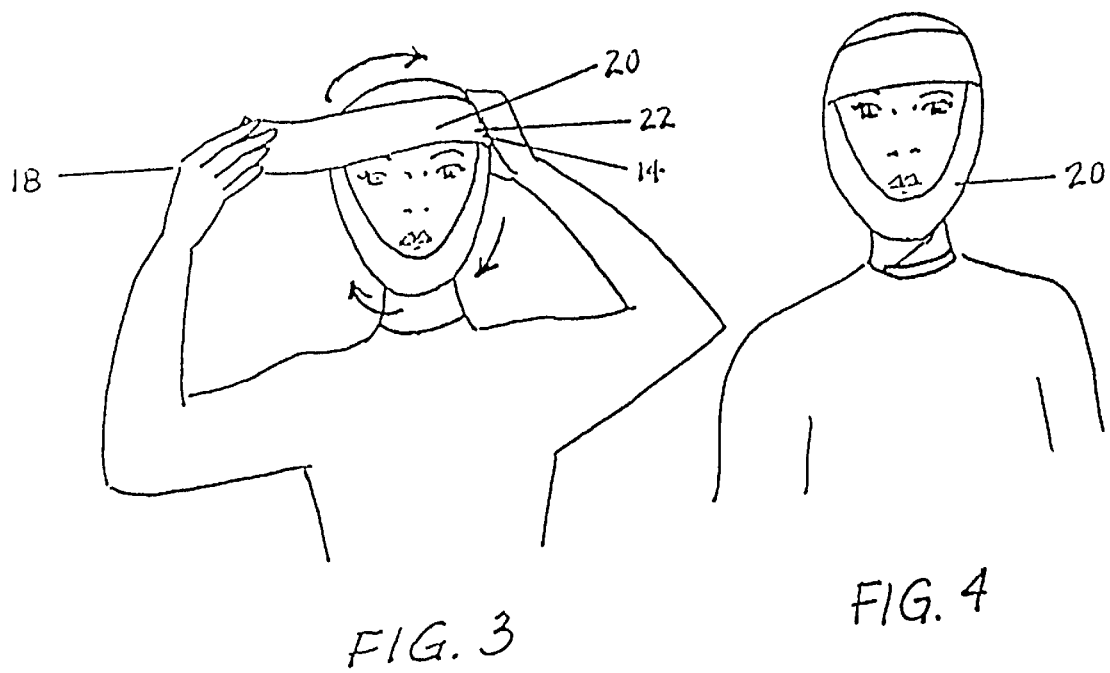
FIG. 3 illustrates the step of applying a second bandage around the forehead in accordance with the invention; and, FIG. 4 shows a fully wrapped head on which the bandages are left in place for a predetermined period of time in accordance with the invention.

A second rolled bandage 20 is held in the right hand and the starting end 22 is held against the forehead with the left hand as shown in FIG. 3. The bandage 20 is unwrapped firmly across the forehead in a direction opposite to the direction in which the first bandage 10 is wrapped in order to smooth frown lines between the brows and on the forehead. Bandage 20 is rolled twice around the head.

After bandage 20 has been rolled around the head twice, it is brought down around the face and over the head once in the opposite direction of the bandage 10. The bandage 20 is finished by wrapping it around the neck and tucking in the loose end to create a head wrap as shown in FIG. 4.

The head wrap is maintained in place for a period of time, no more than 35 minutes. The bandages should not be left on for more than 45 minutes as wrinkles will be created if the bandages lose their tautness. It is possible and desirable to perform a gentle exercise consisting of neck rolls, move the head from side to side, open and close the jaw, chew gum, and/or raise the eyebrows while the head wrap is in place. Any motion should, however, be done without causing any exertion or discomfort.

It is also noted that a mixture of hazelnut oil and/or witch hazel appropriate for a person's age group may be used around the eyes while the head wrap is in place for a more complete treatment. Alternatively, any appropriate eye cream may be used.

After the appropriate period of time has elapsed, the bandages are gently removed by unwrapping them in the direction opposite to the direction in which they were wrapped. A towel is then soaked in hot water, squeezed nearly dry, and applied to the face to soften the mask. The mask is gently removed by wiping with the warm towel or similar cleaning surface.

Once the mask is removed, a cool hydrator or refrigerated witch hazel is applied to the skin to close the pores. The hydrator or witch hazel is preferably applied with a cotton ball.

Following treatment, the face is glowing, age lines are noticeably diminished, and the jawline and neck will be firmer. In short, a subtle, younger look is achieved.

It will thus be seen that the goals set forth above, among those made apparent from the preceeding description, are efficiently attained and, since certain changes may be made in carrying out the above method without departing from the spirit and scope of the invention, it is intended that all matter contained in the above description shall be interpreted as illustrative and not in a limiting sense.

What is claimed is:

1. A method of wrapping a head including a face to diminish age lines, comprising the steps of:
    applying a detoxifying mask to the face;
    wrapping a first elastic bandage around the face;
    pulling the top of the first bandage towards the back of the head;
    applying a second elastic bandage around the forehead and face;
    leaving the bandages in place for a period of time between 30 minutes to 40 minutes;
    performing a gentle exercise selected from the group consisting of head rolls; chewing gum; and raising the eyebrows;
    applying a treatment selected from the group consisting of an eye cream, hazelnut oil, witch hazel, and mixtures thereof around the eyes;
    removing the bandages; and
    removing the mask from the face.

2. The wrapping method of claim 1 wherein the bandages are elasticize Ace® bandages.

3. The method of wrapping of claim 1 wherein the first bandage is rolled around the face and under the chin.

4. The method of wrapping of claim 1 wherein the first wrapped bandage is pulled towards the back of the head using a firm, but gentle motion.

5. The method of wrapping of claim 1 wherein the second wrapped bandage is rolled across the forehead and around the head.

6. The method wrapping of claim 5 wherein the second bandage is wrapped in a direction opposite to the direction in which the first bandage is wrapped.

7. The method of claim 1 wherein the mask is removed using a hot, damp towel.

8. The method of claim 1 further comprising the step of applying a cool hydrator to the face after the mask is removed.

9. The method of claim 1 further comprising the step of applying refrigerated witch hazel to the face after the mask is removed.

* * * * *